(12) United States Patent
Matz et al.

(10) Patent No.: US 11,582,852 B2
(45) Date of Patent: Feb. 14, 2023

(54) SURGICAL LIGHTING SYSTEM THAT REDUCES RISK OF EXCESSIVE RADIANT ENERGY

(71) Applicant: American Sterilizer Company, Mentor, OH (US)

(72) Inventors: Michael K. Matz, Highland Heights, OH (US); Steven T. Moscufo, Davidson, NC (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 17/172,693

(22) Filed: Feb. 10, 2021

(65) Prior Publication Data

US 2022/0256671 A1 Aug. 11, 2022

(51) Int. Cl.
| | |
|---|---|
| *H05B 47/105* | (2020.01) |
| *A61B 90/30* | (2016.01) |
| *H05B 45/10* | (2020.01) |
| *A61B 90/35* | (2016.01) |

(52) U.S. Cl.
CPC ........... *H05B 47/105* (2020.01); *A61B 90/30* (2016.02); *H05B 45/10* (2020.01); *A61B 90/35* (2016.02)

(58) Field of Classification Search
CPC ...... H05B 47/105; H05B 45/10; A61B 90/30; A61B 90/35
See application file for complete search history.

(56) References Cited

U.S. PATENT DOCUMENTS

| | | | |
|---|---|---|---|
| 8,821,017 B2* | 9/2014 | Lalena | A61B 6/4291 378/206 |
| 9,370,079 B2 | 6/2016 | Lashina et al. | |
| 10,271,398 B2 | 4/2019 | Hollopeter et al. | |
| 2012/0279953 A1* | 11/2012 | Augustine | A61F 7/007 219/217 |
| 2015/0094914 A1* | 4/2015 | Abreu | B60H 1/00742 701/41 |

(Continued)

FOREIGN PATENT DOCUMENTS

| | | |
|---|---|---|
| CN | 109640443 A | 4/2019 |
| EP | 3556318 A1 | 10/2019 |

(Continued)

OTHER PUBLICATIONS

Kurwe, M., Karim, H. M. R., Nene, Y., Singh, S., & Ahmed, G. (Jan. 2020). Take extra care of my delicate skin: A lesson from a case of burn from operating room LED top light. Pediatric Anesthesia, 30(1), 78-79.

(Continued)

*Primary Examiner* — Minh D A
(74) *Attorney, Agent, or Firm* — Kusner & Jaffe

(57) ABSTRACT

A light system monitors an area of interest for exposure to radiant energy provided by an operating room light head. At least one operating parameter of the light head is obtained, and based on the at least one operating parameter it is determined if the area of interest has been or will be exposed to radiant energy exceeding a prescribed threshold over a prescribed time period. Based on the determination, the system at least one of automatically adjusts an operating setting of the at least one light head or generates a warning of possible overexposure to radiant energy in the area of interest.

24 Claims, 4 Drawing Sheets

(56) References Cited

U.S. PATENT DOCUMENTS

2018/0124892 A1 5/2018 Hollopeter et al.
2019/0328598 A1 10/2019 Mangiardi

FOREIGN PATENT DOCUMENTS

| FR | 3003011 A1 | 9/2014 | |
|---|---|---|---|
| JP | 2015035373 A | 2/2015 | |
| WO | WO-2015006872 A1 * | 1/2015 | ............... A61N 5/06 |
| WO | WO-2018/231887 A1 | 12/2018 | |
| WO | WO-2019/190967 A1 | 10/2019 | |
| WO | WO-2020/084611 A1 | 4/2020 | |

OTHER PUBLICATIONS

Bates, J., Hall, A., Kunanandam, T., & Hewitt, R. (2018). Otological surgery in paediatric photosensitive patients. *International journal of pediatric otorhinolaryngology*, 115, 175-176.
International Search Report and Written Opinion issued in related International Application No. PCT/US2022/014867 dated Jun. 1, 2022.

* cited by examiner

SURGICAL LIGHTING SYSTEM THAT REDUCES RISK OF EXCESSIVE RADIANT ENERGY

FIELD OF THE INVENTION

The present invention relates generally to surgical lighting systems and, more particularly, to a method and apparatus for monitoring one or more operating parameters of a surgical lighting system or one or more quantities of the immediate surgical environment and, based on the monitored parameters, respond in a way that reduces the risk of harm to a patient due to excessive radiant exposure.

BACKGROUND OF THE INVENTION

Surgical lights are typically designed to be as bright as allowed by safety standards. These safety standards only limit the brightness of a single surgical light with no regard for the accumulated effect of the radiant power, e.g. the radiant energy emitted by each light in combination with the length of time the light has been on and/or on the patient, the increased radiant power delivered to a surgical site due to multiple lights being aimed at the same surgical site, etc. It is common clinical practice to use a surgical lighting system at full intensity for the duration of a procedure, which exposes a patient to radiant energy that could, over time, dry out the patient's exposed tissue, or could possibly cause an even worse adverse effect. The FDA has received multiple reports of over-exposure from surgical lights resulting in discoloration or burning of patient's skin. Although the Instructions for Use (Operator's Manual) may warn of the risks of excessive radiant power, and users are able to decrease the radiant power as they wish, there are no known surgical lighting products that automatically reduce the radiant power in response to any measured or input quantity or warn the user to consider doing so. The responsibility for preventing such adverse events currently rests entirely on the surgical team.

SUMMARY OF THE INVENTION

In accordance with the invention, operating parameters of a surgical lighting system alone or in combination with environmental parameters, patient information and/or procedure information is/are used to either warn surgical staff of a specific risk of harm to the patient due to excessive radiant exposure, or reduce risk of harm to the patient by automatically adjusting operating parameters of the surgical lighting system to reduce an amount of radiant energy subjected to the area of interest.

An advantage of the device and method in accordance with the invention is that patient safety is enhanced due to decreased risk of photobiological damage from excessive radiant exposure during a procedure.

According to one aspect of the invention, an operating light includes: at least one light head including at least one light-emitting element for illuminating an area of interest; and a controller communicatively coupled to the at least one light head, the controller configured to obtain operating parameters of the at least one light head, based on the operating parameters, determine if the area of interest has been or will be exposed to radiant energy exceeding a prescribed threshold over a prescribed time period, and based on the determination, at least one of automatically adjust an operating setting of the at least one light head or generate a warning of possible overexposure to radiant energy in the area of interest.

In one embodiment, the controller is configured to calculate a dosage of radiant energy provided by the light head to the area of interest.

In one embodiment, the controller is configured to calculate the dosage based on a radiant power output of each of the at least one light-emitting element, a distance of the at least one light emitting element from the area of interest, a size of the illuminated area, and a time period over which the at least one light emitting element is illuminated.

In one embodiment, the controller is configured to compare the calculated dosage to a prescribed dosage, and upon the calculated dosage exceeding the prescribed dosage, modify the operating setting of the light head.

In one embodiment, the radiant energy comprises visible light, infra-red light or ultraviolent light.

In one embodiment, the at least one operating parameter comprises at least one of a duration of use of the at least one light-emitting element, a radiant power output by the at least one light-emitting element, a size and shape of light on the area of interest, or a distance of the at least one light head from the area of interest.

In one embodiment, the operating light includes at least one sensor communicatively coupled to the controller, the at least one sensor operative to monitor at least one characteristics of the area of interest, wherein the controller is configured to alter the output setting of the light head based on the monitored at least one characteristics of the area of interest.

In one embodiment, wherein the controller is configured to determine energy reflected from the area of interest or co-illumination of the area of interest based on data provided by the at least one sensor.

In one embodiment, the at least one sensor comprises at least one of a light detection sensor, a temperature sensor, or a humidity sensor.

In one embodiment, the controller is configured to calculate the prescribed threshold level based on patient data of a patient to be placed in the area of interest.

In one embodiment, the patient data comprise at least one of an age, gender or ethnicity of a patient.

In one embodiment, the patient data comprises at least one of a skin pigmentation of a patient, a medical history of the patient, a type of a medical procedure to be performed on the patient, or duration of a medical procedure to be performed on the patient.

In one embodiment, the controller is configured to generate a risk index for the patient based on at least one of the at least one operating parameter of the light head or the patient data.

According to another aspect of the invention, a method of monitoring an area of interest for exposure to radiant energy provided by an operating room light head includes: obtaining at least one operating parameter of the light head, based on the at least one operating parameter, determining if the area of interest has been or will be exposed to radiant energy exceeding a prescribed threshold over a prescribed time period, and based on the determination, at least one of automatically adjusting an operating setting of the at least one light head or generating a warning of possible overexposure to radiant energy in the area of interest.

In one embodiment, the method includes calculating a dosage of radiant energy provided by the light head to the area of interest.

In one embodiment, calculating the dosage includes calculating the dosage based on a radiant power output by each of the at least one light-emitting element, a distance of the at least one light emitting element from the area of interest, the size and shape of the illuminated area, and a time period over which the at least one light emitting element is illuminated.

In one embodiment, the method includes comparing the calculated dosage to a prescribed dosage, and upon the calculated dosage exceeding the prescribed dosage, modifying the operating setting of the light head.

In one embodiment, the at least one operating parameter comprises at least one of a duration of use of the light head, a radiant power output by the light head, a pattern of light on the area of interest, or a distance of the light head from the area of interest.

In one embodiment, the method includes: monitoring at least one characteristics of the area of interest; and altering the output setting of the light head based on the monitored at least one characteristic of the area of interest.

In one embodiment, the controller is configured to determine energy reflected from the area of interest or co-illumination of the area of interest based on data provided by the at least one sensor.

In one embodiment, the method includes calculating the prescribed threshold level based on patient data of a patient to be placed in the area of interest.

In one embodiment, the patient data comprise at least one of an age, gender or ethnicity of a patient.

In one embodiment, the patient data comprises at least one of a skin pigmentation of a patient, a medical history of the patient, a type of a medical procedure to be performed on the patient, or duration of a medical procedure to be performed on the patient.

In one embodiment, the method includes generating a risk index for the patient based on at least one of the at least one operating parameter of the light head or the patient parameters.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
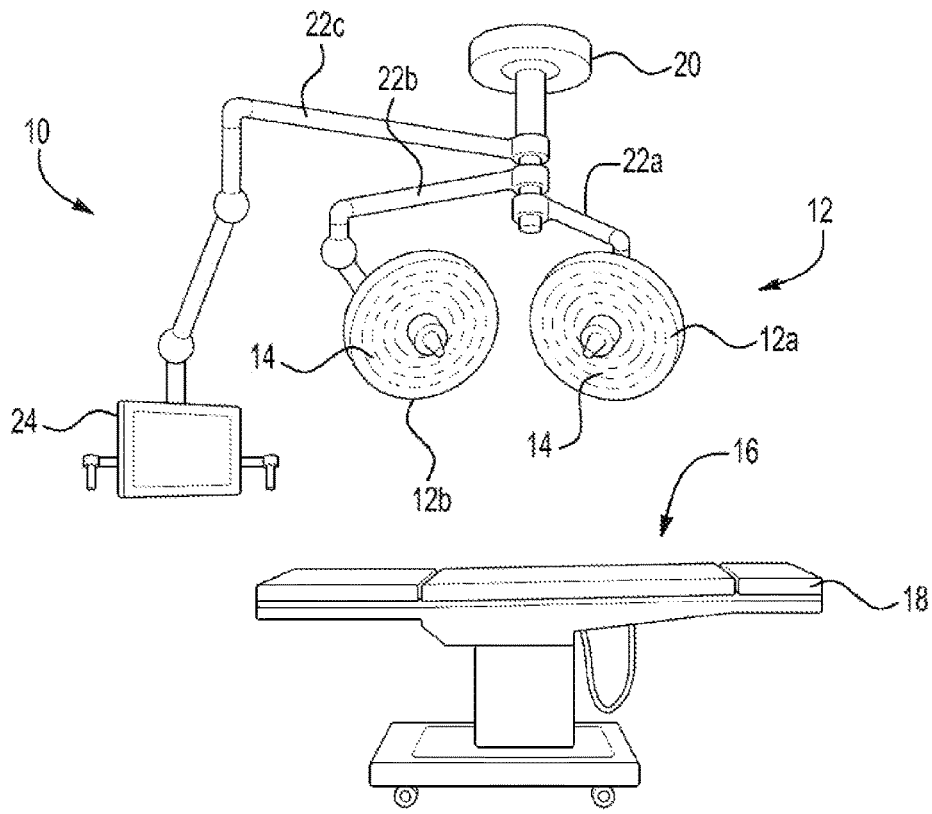
FIG. 1 is a perspective view of an exemplary medical light system in accordance with an embodiment of the invention.

Embodiments of the present invention will now be described with reference to the drawings, wherein like reference numerals are used to refer to like elements throughout. It will be understood that the figures are not necessarily to scale.

The methods and devices in accordance with the present invention have particular utility in operating room lighting systems and, thus, the embodiments are described chiefly in this context. However, aspects of the invention are applicable to other lighting systems. For example, aspects of the invention are applicable to sun lamps, tanning beds and the like.

Many of the elements discussed in this specification, whether referred to as a 'system' a 'module' a 'circuit' or similar, may be implemented in hardware circuit(s), a processor executing software code, or a combination of a hardware circuit and a processor executing code."

As used herein, the term "radiant energy" is defined as the energy of electromagnetic radiation including energy in the visible and/or invisible (infrared, ultraviolet) portion of the spectrum, and may be expressed as Joules (J). Additionally, the term "radiant power" is defined as the radiant energy emitted, reflected, transmitted or received per unit of time, and may be expressed as watts (W or J/s). Further, the term "radiant exposure" is defined as the radiant energy received by a surface per unit area and may be expressed as Joules/square meter ($J/m^2$).

In accordance with aspects of the invention, a lighting system monitors one or more operational parameters and/or one or more quantities of the immediate environment and, based on the monitored parameters and/or quantities, responds in a way that reduces the risk of harm to the patient due to excessive radiant exposure. Furthermore, this response may be based on known information about the patient and/or the procedure performed on the patient, each of which may be input to the system by a user, such as a medical professional. Non-limiting examples of operating parameters that may be monitored include duration of use of the light head, an intensity (power) setting of light emitted by the light head, a shape of the light pattern on the area of interest (e.g., circular, oblong), a size of the area illuminated by the light head, and a distance of the light head from the area of interest. As will be appreciated, other parameters may be monitored by the system without departing from the scope of the invention.

The lighting system in accordance with the invention may calculate additional quantities based on the parameters. For example, an effective dosage may be calculated, where the dosage is based on a combination of the duration over which the area of interest is illuminated, the distance of the light head 12 from the area of interest, the number of light heads 12 directed toward the area of interest 16, and the radiant power emitted by each light head 12. Other parameters may be considered in determining if a patient in the area of interest is subjected to excessive radiant exposure. For example, environmental parameters of the surgical environment (e.g., a temperature of the area of interest and/or a temperature of a patient in the area of interest, a humidity of air in the area of interest) may be considered in determining if the patient is or may be subjected to excessive radiant exposure. In this regard, the temperature of the patient's skin or of the exposed surgical site (e.g., an open cut or wound) may be monitored, and if the temperature exceeds a prescribed threshold value it may be concluded that the patient has been subjected to excessive radiant exposure. Co-illumination of the patient and/or the area of interest and/or reflected energy from the patient/area of interest may also be considered, where such co-illumination and/or reflected energy may indicate the patient/area of interest is exposed to radiant energy from a source other than the light head. Such co-illumination may be detected based on sensor measurements in combination with known settings of the light head, wherein if detected radiant power is greater than expected radiant power it may be concluded that the additional radiant power is due to co-illumination. Based on the detected co-illumination and/or reflected energy, the amount of radiant energy provided to the patient/area of interest may be revised to reflect radiant energy from unknown and/or unaccounted sources.

In calculating additional quantities, such as dosage of radiant energy provided by the light head to the area of interest, over exposure to radiant energy, etc., additional factors may be taken into account. These factors can include the patient's age, gender, skin pigmentation, history (including medications and/or photosensitivity) and like characteristics. The patient factors then can be used to access a database to retrieve settings for the system, such as maximum dosage, recommended settings for the light head, a risk index for over exposure using specific settings, etc. Additionally, the type of procedure being performed may be a factor that is used to search the database. In this regard, the type of procedure may be indicative of an expected time required to conduct the procedure, an expected radiant power of the light head used during the procedure, a number of light heads to be used during the procedure, etc.

As briefly noted above, a risk index and a risk threshold can be calculated based on one or more of the above factors. A comparison between the calculated risk index and risk threshold then can be made and, based on the comparison, appropriate action can be taken. For example, if the risk index exceeds the risk threshold the lighting system can respond to reduce the risk of harm to the patient. Such response may include warning the user of the risk via visual or audible means, such as text on a monitor, flashing lights, changing colors, voice recording or synthesized voice, alarm bells, etc. Additionally or alternatively, the system may automatically reduce the light intensity (power) and/or store data in electronic medical records (EMRs) of the patient. For example, the system, upon detecting the risk index will or has exceeded the risk threshold, the dosage exceeds a high limit, or other monitored parameter has exceeded a prescribed threshold level, then the intensity (power) of the light emitted from each light head can be reduced to 50% of maximum.

Referring now to FIG. 1, illustrated is an exemplary operating light 10 in accordance with the invention. The operating light 10 includes one or more light heads 12 each including one or more lighting elements 14 for illuminating an area of interest 16, such as an area over an operating table 18. In the illustrated embodiment, the surgical lighting system 10 includes two light heads 12a, 12b, each light head including a plurality of light emitting elements 14 in the form of LED modules. While LED modules are preferred due to their low power consumption and minimal ultraviolet light emissions, it will be appreciated that other types of light emitting elements may be utilized within each light head 12a, 12b. Each light head 12a, 12b may be secured to a support, such as a ceiling or wall within an operating room via a support base 20 and articulating arms 22a, 22b.

A controller 24 is communicatively coupled to each light head 12a, 12b so as to monitor and/or control parameters of each light head 12a, 12b. In the exemplary embodiment shown in FIG. 1 the controller 24 includes a display and interface portion (e.g., a touch screen or the like), and circuitry (not shown) such as a microprocessor and memory that are operable to execute instructions stored in the memory, and/or an application-specific integrated circuit (ASIC) configured to carry out specific instructions. The controller 24 also may be mounted to the base support 20 via articulating arm 22c. It will be appreciated, however, that the controller 24 may be split into multiple modules, where a first module having control functions is mounted remote from the light heads 12a, 12b, and a second module having the display and interface functions is mounted at or near the light heads 12a, 12b (e.g., on the articulated arm 22c). For example, a first module may have a processor, memory and instructions stored in the memory, the first module residing on a table, cart or otherwise remote from the light heads 12a, 12b (e.g., in a different area or room from the light heads). The first module may communicate with the second module (which may be in the form of a user interface 24a as discussed below) and the light heads 12a, 12b either wirelessly or through a wired connection.

Regardless of the configuration of the controller 24, in communicating with the light heads 12 the controller 24 obtains operating parameters of the respective light heads 12. As previously noted, the operating parameters include, for example, an intensity (power) setting for each light head 12a, 12b and/or each light emitting element 14, an intended duration of use of each light head 12a, 12b or light emitting element 14, a direction of each light head 12a, 12b and/or light emitting element 14, and so forth. The controller 24 determines if the area of interest 16 will be or has been subjected to excessive radiant exposure (e.g., based on the operating parameters it is determined if the surface area may be or has been exposed to radiant energy exceeding a prescribed threshold over a prescribed time period). If it is determined that excessive radiant exposure is possible or has occurred, action is taken by the controller 24. For example, an operating setting of one or all light heads 12 may be automatically adjusted to minimize the chance of over exposure. Alternatively or additionally, a warning may be output on a display of the controller 24 to alert medical personnel of possible over exposure to radiant energy in the area of interest.

Figure 2:
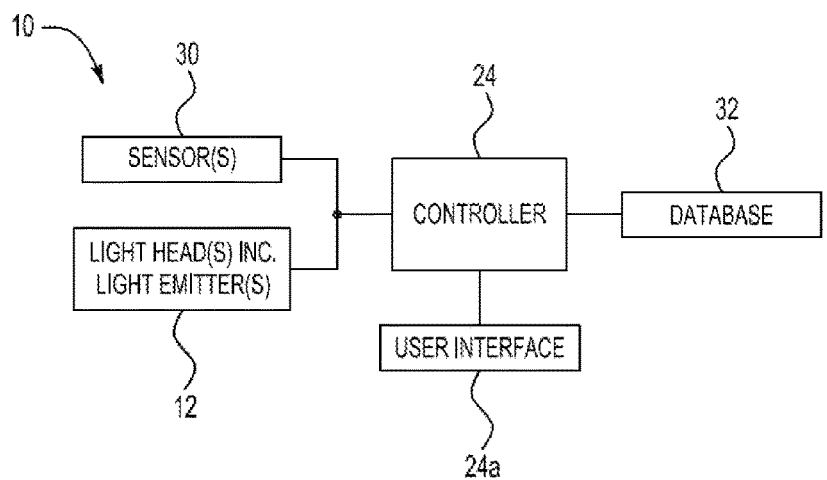
FIG. 2 is a block diagram illustrating components of an exemplary medical light system in accordance with an embodiment of the invention.

With additional reference to FIG. 2, a block diagram is provided that shows additional features of the system 10. As previously noted, the controller 24 is communicatively coupled to the light heads 12 via a wired or wireless connection. A user interface 24a is also communicatively coupled to the controller 24. The user interface 24a, which may be in the form of a graphical user interface on a display, enables medical personnel to adjust settings of the light heads 12, view current settings of the light head, view patient and procedure data, view accumulated exposure data, output warnings/alarms, and the like.

The system can further include one or more sensors 30 communicatively coupled to the controller 24. The sensors 30 are operative to monitor one or more characteristics of the area of interest 16 and/or patient in the area of interest and provide data to the controller 24 for analysis. Various sensors may be used depending on the requirements of the system. For example, the sensors 30 may be in the form of a light detection sensor, a temperature sensor, a humidity sensor, or any sensor that can measure a property of the area of interest 16 and/or of a patient in the area of interest 16. As described in more detail below, the data from the sensors 30 can be used by the controller 24 to determine the risk of over exposure to radiant energy and to compensate for such over exposure.

Also communicatively coupled to the controller 24 is a database 32. The database 32, which may be integral with the controller 24 or remote from the controller, includes various data related to medical procedures, patient characteristics, dosage for various light intensities and distance of the light head to the area of interest, threshold levels, and the like. Based on settings of the light head 12, patient characteristics, procedure characteristics, etc., the controller 24 can access the database 32 and retrieve information that can be used to calculate thresholds, expected dosage levels, alarm/warning set points, and the like.

Figure 3:
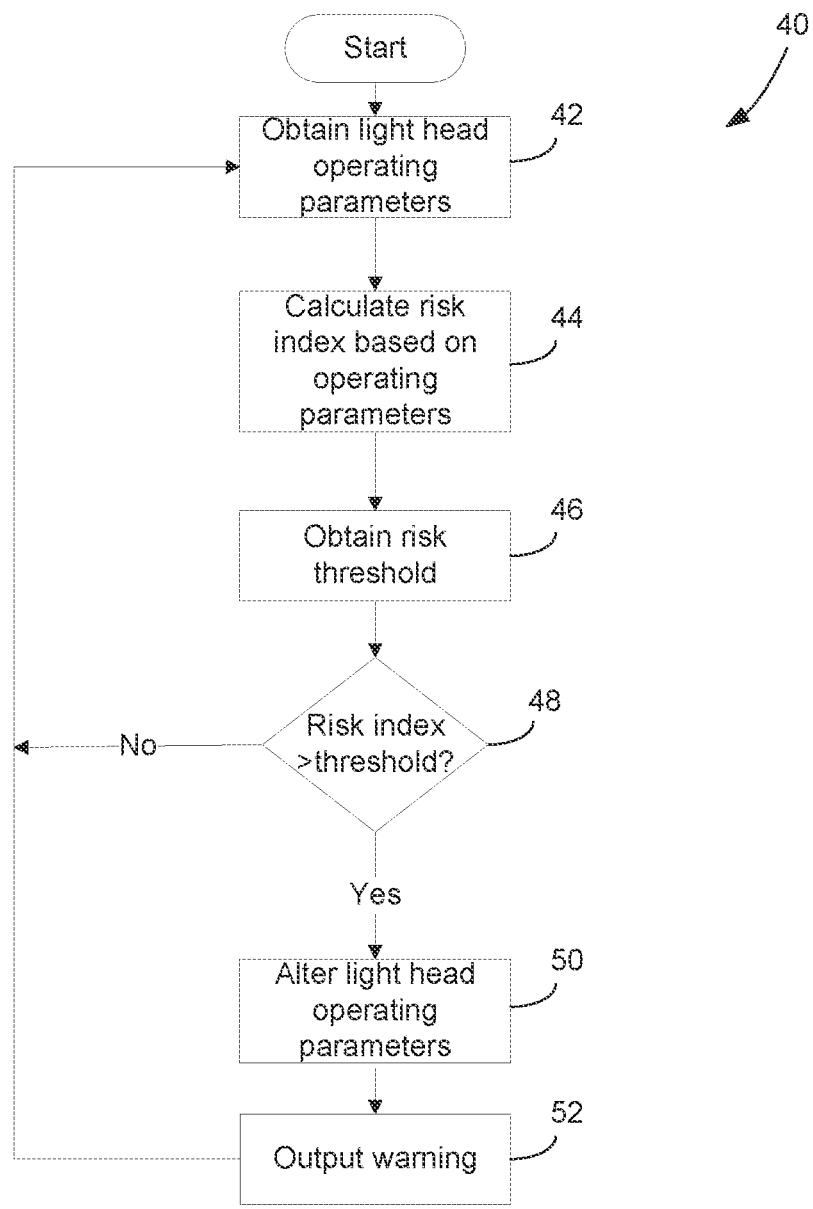
FIG. 3 is a flow chart illustrating an exemplary method of operating a medical light system in accordance with an embodiment of the invention.
Figure 4:
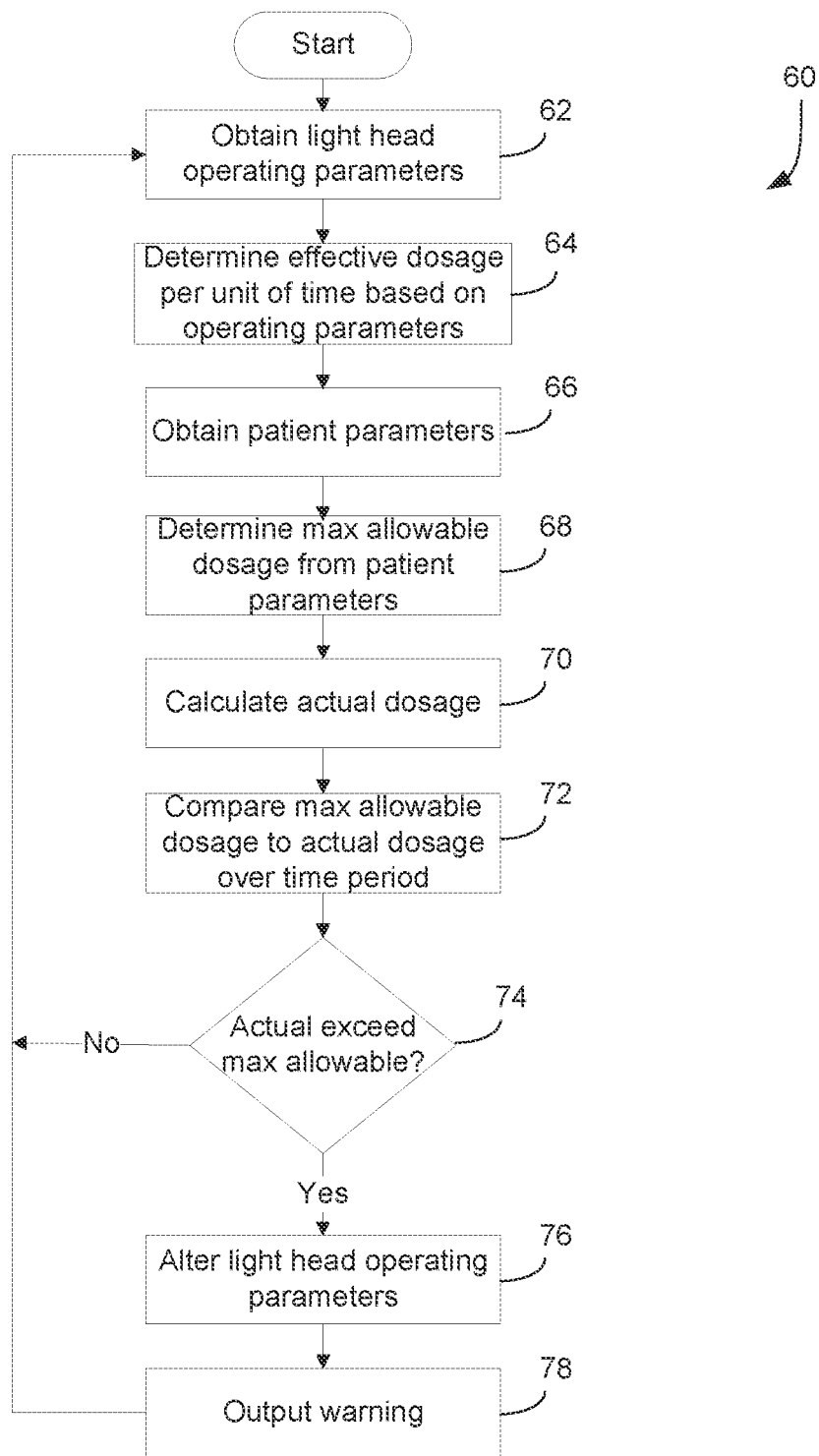
FIG. 4 is a flow chart illustrating an exemplary method of operating a medical light system in accordance with another embodiment of the invention.
Figure 5:
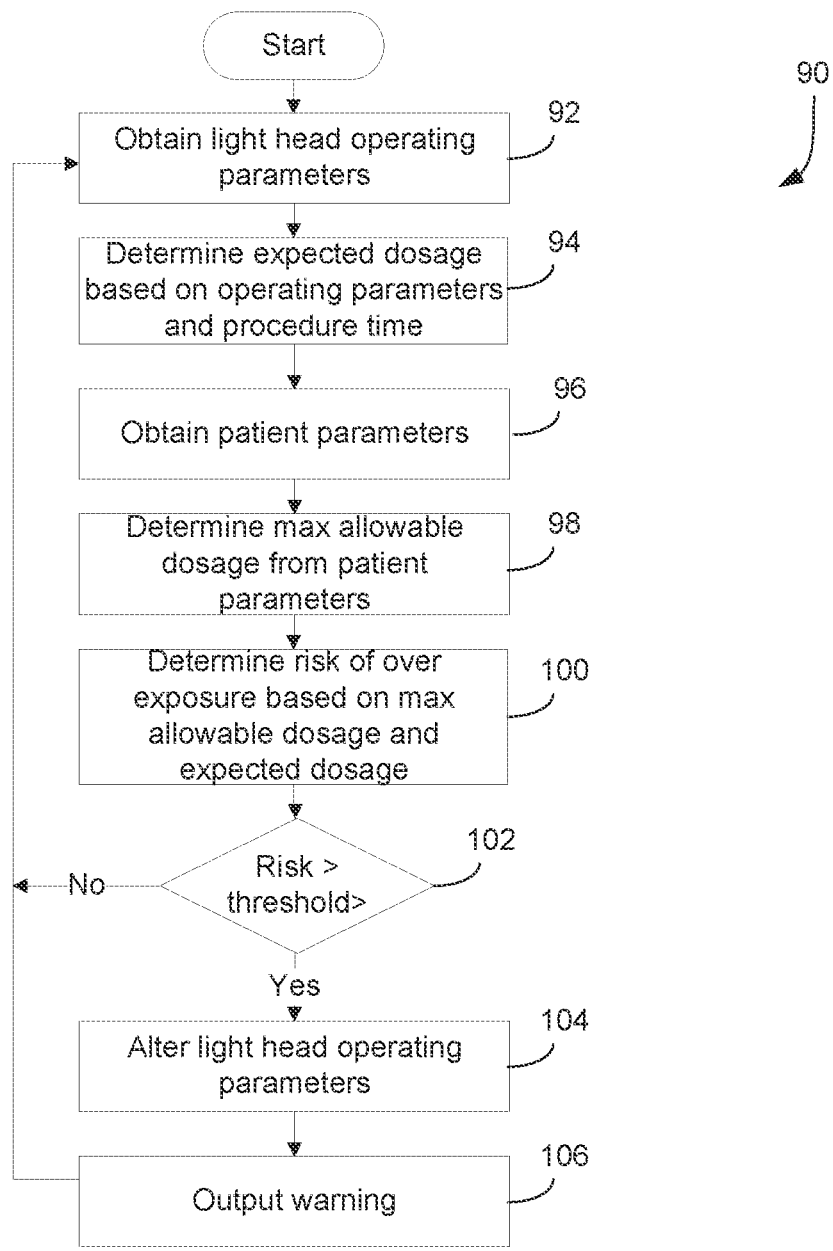
FIG. 5 is a flow chart illustrating an exemplary method of operating a medical light system in accordance with an embodiment of the invention.

Moving now to FIGS. 3-5, illustrated are exemplary methods of implementing a light system in accordance with the invention. Variations to the illustrated methods are possible and, therefore, the illustrated embodiments should not be considered the only manner of carrying out the techniques that are disclosed in this document. Also, while FIGS. 3-5 show a specific order of executing functional logic blocks, the order of executing the blocks may be changed relative to the order shown and/or may be implemented in an object-oriented manner or a state-oriented manner. In addition, two or more blocks shown in succession may be executed concurrently or with partial concurrence. Certain blocks also may be omitted.

The exemplary method may be carried out, for example, by executing code stored by an electronic device. The code may be embodied as a set of logical instructions that may be executed by a processor. Therefore, the methods may be embodied as software in the form of a computer program that is stored on a computer readable medium. The term "computer-readable medium" as used herein refers to any medium that participates in providing instructions to a processor for execution. Such a medium may take many forms, including but not limited to, non-volatile media and volatile media. Non-volatile media includes, for example, optical or magnetic disks, or non-volatile read-only memory. Volatile media includes dynamic memory.

Referring to FIG. 3, illustrated is a method 40 for operating a lighting system in accordance with one embodiment of the invention. Beginning at step 42, the controller 24 obtains operating parameters of the light head(s) 12. These parameters may be obtained, for example, from memory of the controller 24 (which may command the light head to utilize particular settings), or by querying the light head 12 for the current operating settings of the light heads 12. Exemplary operating parameters include a duration of use of the light head 12, the radiant power setting of the light head 12, a pattern of light on the area of interest 16, or a distance of the at least one light head 12 from the area of interest 16.

Next at step 44 the controller 24 calculates a risk index based on the operating parameters of the light head(s) 12. In the embodiment of FIG. 3, the risk index may be calculated based on an expected total radiant exposure subjected to the area of interest 16, where the risk index may be a numerical value having a low (minimal risk) and high (significant risk) value (e.g., a risk index of 0 being minimal risk and a risk index of 100 being significant risk, and values therebetween having corresponding levels of risk). For example, based on the radiant power that each light head 12 is expected to emit while operating at the specified settings in combination with a distance of each light head 12 from the area of interest 16 and the expected exposure time, the radiant exposure subjected to the area of interest 16 can be approximated. Higher risk may be associated with higher radiant power outputs from the light heads 12 and less distance between the light head 12 and the area of interest 16, while lower risk may be associated with lower radiant power outputs from the light heads 12 and greater distance between the light head 12 and the area of interest 16.

Next at step 46 a risk threshold is obtained, for example, from the database 32. The risk threshold can be a numerical value representative of an acceptable level of risk (where "acceptable" implies the risk is below a risk threshold established by the manufacturer during risk assessment). A risk index below the risk threshold is considered low risk and a risk index above the threshold is considered high risk. At step 48 it is determined if the risk index as determined in step 44 exceeds the risk threshold obtained in step 46. If the risk index does not exceed the risk threshold, then it is concluded that the area of interest/patient will not be subjected to excessive radiant exposure and the method moves back to step 42. If the risk index exceeds the risk threshold, then the method moves to steps 50 and 52.

At step 50, the controller 24 may recommend or automatically adjust operating parameters of the light heads 12 in order to bring the risk index at or below the risk threshold. For example, the controller 24, knowing the risk threshold, the distance of the light heads from the area of interest, the number of light heads 12 and the radiant power produced by each light head, and the expected duration of exposure, can calculate a radiant power setting for the light heads 12 that produces a risk index at or below the risk threshold. The controller 24 may automatically adjust the parameters of the light heads 12 or may request confirmation of any changes to the system settings via the user interface 24a. Further, the controller 24 may output a visual and/or audible warning/alarm on the user interface 24a as indicated at step 52. The method then moves back to step 42 and repeats.

Moving now to FIG. 4, illustrated is a method 60 for operating a lighting system in accordance with another embodiment of the invention. Beginning at step 62, and similar to step 42 of the method of FIG. 3, the controller 24 obtains operating parameters of the light head(s) 12 (e.g., a duration of use of each light head 12, a radiant power setting of each light head 12, a pattern of light on the area of interest 16, or a distance of each light head 12 from the area of interest 16). The parameters can be obtained, for example, from memory of the controller 24 or by querying the light head 12 for current operating settings of the light heads 12.

Next at step 64 the controller 24 determines an effective dosage provided to the area of interest 16 based on the operating parameters of the light heads 12. For example, based on the radiant power emitted by each light head 12 and the distance of each light head 12 from the area of interest 16, the dosage of radiant energy received in the area of interest 16 over a prescribed time period (e.g., 1 second, 1 minute) can be calculated. This information then is used in a subsequent step to determine the effective dosage delivered to the area of interest 16 and/or a patient in the area of interest 16.

Next at step 66 the controller 24 obtains patient data for the patient that is to undergo treatment. The patient data may be obtained from the controller 24, the data being entered into the system via the user interface 24a and/or via other means. Alternatively, the patient data may be obtained from the database 32 or from an electronic patient chart (not shown). Exemplary patient data can include one or more of age, gender, ethnicity, skin pigmentation, medical history, the type of a medical procedure to be performed on the patient, or duration of a medical procedure to be performed on the patient.

Using the patient data obtained in step 66, the controller 24 determines a maximum recommended dosage of radiant energy for the patient, as indicated at step 68. In this regard, the controller 24 may use the patient data as criteria for retrieving from the database 32 the maximum recommended dosage. In its simplest form, a lookup table or like data storage may contain a large number of different patient data, and a maximum dosage entry is associated with each combination of patient data. The maximum recommended dosage for each combination of patient data may be based on clinical experience and/or a clinical study. Thus, for example, from clinical experience and/or a clinical study it may be determined that for a white male between 55 and 60 years of age with normal skin pigmentation, no medical history of sensitivity to radiant light energy and undergoing an arthroscopic procedure, the recommended maximum dosage of radiant energy is 11 $MJ/m^2$. Similarly, for a white male between 25 and 30 years of age with normal skin pigmentation, no medical history of sensitivity to radiant light energy and undergoing an arthroscopic procedure, the recommended maximum dosage is 12 $MJ/m^2$. The recommended maximum dosage for each combination of patient data can be assembled and entered in the lookup table for the corresponding combination of patient data. As will be appreciated, due to the significant number of possible combinations of patient data the number of entries in the lookup table can be large. To help reduce the number of entries, the span between entries may be widened and a form of smoothing (e.g., linear interpolation or other extrapolation methodology) may be implemented to obtain a recommended dosage for patient data that falls between entries in the lookup table. For example, instead of including entries for each year of a patient's age (e.g., 30, 31, 32, 33, 34, 35, etc.), entries may only be included at intervals of 5 years of age (e.g., 30, 35, 40, etc.). Then, for a patient having an age falling between 30 and 35 years, smoothing may be utilized to extrapolate a recommended maximum dosage based on the corresponding recommended maximum dosage for a 30-year old patient and for a 35-year old patient.

At step 70, the controller 24 calculates the actual dosage delivered to the area of interest 16 or patient in the area of interest. In this regard, the actual dosage may be calculated by integrating the radiant power provided by the light head(s) 12 (at the obtained operating parameters—(exposure duration, intensity, light pattern size, etc.) with respect to time. The radiant power may be calculated based on the obtained parameters of the light head 12 and/or based on data provided by one or more sensors 30 (e.g., the light intensity output by each light head 12, the distance of each light head 12 to the area of interest 16). By integrating the radiant power provided to the area of interest 16 over time, the dosage of radiant energy provided to the area of interest/patient can be precisely determined.

Next at step 72 the actual dosage as determined in step 70 is compared to the maximum recommended dosage as determined at step 68, and at step 74 it is determined if the actual dosage exceeds the maximum recommended dosage. If the actual dosage does not exceed the maximum recommended dosage, then the method moves back to step 62. If the actual dosage exceeds the maximum recommended dosage, then the method moves to steps 76 and 78.

At step 76, the controller 24 may recommend or automatically adjust operating parameters of the light heads 12 in order to reduce any further radiant exposure to the area of interest/patient. For example, the controller 24 may automatically reduce the light output (reduce the radiant power) by one or both light heads 12 by a predetermined percentage, and/or output to the user interface 24a a recommended change in settings of the light head's operating parameters. The controller 24 may automatically make changes to the system settings or may request confirmation of any changes to the system settings via the user interface 24a. Further, the controller 24 may output a visual and/or audible warning/alarm on the user interface 24a as indicated at step 78. The method then moves back to step 62 and repeats.

Moving now to FIG. 5, illustrated is a method 90 for operating a lighting system in accordance with another embodiment of the invention. As will be seen below, the method of FIG. 5 incorporates parts of each of the method of FIGS. 3 and 4.

Beginning at step 92, and similar to steps 42 and 62 of the method of FIGS. 3 and 4, the controller 24 obtains operating parameters of the light head(s) 12 (e.g., a duration of use of the light head 12, a radiant power setting of each light head, a pattern of light on the area of interest 16, or a distance of each light head from the area of interest 16). The parameters can be obtained, for example, from memory of the controller 24 or by querying the light head 12 for current operating settings of the light heads 12.

Next at step 94 the controller 24 determines an expected dosage provided to the area of interest 16 based on the operating parameters of the light heads 12. For example, based on the radiant power of each light head 12, the distance of each light head from the area of interest 16, and an expected duration of the procedure, the dosage of radiant energy received in the area of interest can be calculated.

Moving to step 96 the controller 24 obtains patient data for the patient that is to undergo treatment. The patient data may be obtained from the controller 24, which may have been entered into the system via the user interface 24a or other means. Alternatively, the patient data may be obtained from the database 32 or from an electronic patient chart (not shown). Exemplary patient data can include one or more of age, gender, ethnicity, skin pigmentation, medical history, a type of a medical procedure to be performed on the patient, or duration of a medical procedure to be performed on the patient.

Using the patient data obtained in step 96, the controller 24 determines a maximum allowable dosage of radiant energy for the patient, as indicated at step 98. In this regard, the controller 24 may use the patient data as criteria for retrieving data from the database 32 to determine a maximum dosage for the patient.

At step 100, the controller 26 compares the maximum allowable dosage to the expected dosage and formulates a risk index. For example, the risk index may be expressed as the ratio of the expected dosage to the maximum allowable dosage. A ratio of less than 0.6 may be regarded as little risk, a ratio between 0.6 and 0.9 may be regarded as a moderate risk, and ratios of 0.9 and over may be regarded as a high risk. As will be appreciated, the various ranges for low, medium and high risk may be changed to fit the patient factors and/or factors associated with the procedure to be performed.

Next at step 102 if the risk index is less than a predetermined risk index threshold, then the method moves back to step 92. If the risk index is equal to or greater than the predetermined risk index, then the method moves to steps 104 and 106.

At step 104, the controller 24 may recommend or automatically adjust operating parameters of the light heads 12 in order to reduce any further radiant exposure to the area of interest/patient. For example, the controller 24 may automatically reduce the light intensity (power) by one or both light heads 12 by a predetermined percentage, and/or output to the user interface 24a a recommended change in settings of the light head's operating parameters. The controller 24 may automatically make these changes or may request confirmation of any changes via the user interface 24a. Further, the controller 24 may output a visual and/or audible warning/alarm on the user interface 24a as indicated at step 106. The method then moves back to step 92 and repeats.

The lighting system and method in accordance with the present invention can predict and/or actively monitor radiant exposure to an area of interest. Advantageously, in the event of excessive radiant exposure the system can automatically modify lighting parameters and/or can alert a user of potential excessive radiant exposure to a patient or area of interest.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

What is claimed is:

1. An operating light, comprising:
   at least one light head including at least one light-emitting element for illuminating an area of interest; and
   a controller communicatively coupled to the at least one light head, the controller configured to
      obtain operating parameters of the at least one light head,
      based on the operating parameters, determine i) if the area of interest has been exposed to radiant energy exceeding a prescribed threshold over a prescribed time period or ii) if the area of interest will be exposed to radiant energy exceeding the prescribed threshold over the prescribed time period, and
      based on the determination, at least one of automatically adjust an operating setting of the at least one light head or generate a warning of possible overexposure to radiant energy in the area of interest.

2. The operating light according to claim 1, wherein the controller is configured to calculate a dosage of radiant energy provided by the light head to the area of interest.

3. The operating light according to claim 2, wherein the controller is configured to calculate the dosage based on a radiant power output of each of the at least one light-emitting element, a distance of the at least one light emitting element from the area of interest, a size of the illuminated area, and a time period over which the at least one light emitting element is illuminated.

4. The operating light according to claim 2, wherein the controller is configured to compare the calculated dosage to a prescribed dosage, and upon the calculated dosage exceeding the prescribed dosage, modify the operating setting of the light head.

5. The operating light according to claim 4, wherein the radiant energy comprises visible light, infra-red light or ultraviolent light.

6. The operating light according to claim 1, wherein the at least one operating parameter comprises at least one of a duration of use of the at least one light-emitting element, a radiant power output by the at least one light-emitting element, a size and shape of light on the area of interest, or a distance of the at least one light head from the area of interest.

7. The operating light according to claim 1, further comprising at least one sensor communicatively coupled to the controller, the at least one sensor operative to monitor at least one characteristics of the area of interest, wherein the controller is configured to alter the output setting of the light head based on the monitored at least one characteristics of the area of interest.

8. The operating light according to claim 7, wherein the controller is configured to determine energy reflected from the area of interest or co-illumination of the area of interest based on data provided by the at least one sensor.

9. The operating light according to claim 7, wherein the at least one sensor comprises at least one of a light detection sensor, a temperature sensor, or a humidity sensor.

10. The operating light according to claim 1, wherein the controller is configured to calculate the prescribed threshold level based on patient data of a patient to be placed in the area of interest.

11. The operating light according to claim 10, wherein the patient data comprise at least one of an age, gender or ethnicity of a patient.

12. The operating light according to claim 10, wherein the patient data comprises at least one of a skin pigmentation of a patient, a medical history of the patient, a type of a medical procedure to be performed on the patient, or duration of a medical procedure to be performed on the patient.

13. The operating light according to claim 10, wherein the controller is configured to generate a risk index for the patient based on at least one of the at least one operating parameter of the light head or the patient data.

14. A method of monitoring an area of interest for exposure to radiant energy provided by an operating room light head, comprising:
   obtaining at least one operating parameter of the light head,
   based on the at least one operating parameter, determining i) if the area of interest has been exposed to radiant energy exceeding a prescribed threshold over a prescribed time period or ii) if the area of interest will be exposed to radiant energy exceeding the prescribed threshold over the prescribed time period, and
   based on the determination, at least one of automatically adjusting an operating setting of the at least one light head or generating a warning of possible overexposure to radiant energy in the area of interest.

15. The method according to claim 14, further comprising calculating a dosage of radiant energy provided by the light head to the area of interest.

16. The method according to claim 15, wherein calculating the dosage includes calculating the dosage based on a radiant power output by each of the at least one light-emitting element, a distance of the at least one light emitting element from the area of interest, the size and shape of the illuminated area, and a time period over which the at least one light emitting element is illuminated.

17. The method according to claim 15, further comprising comparing the calculated dosage to a prescribed dosage, and upon the calculated dosage exceeding the prescribed dosage, modifying the operating setting of the light head.

18. The method according to claim 14, wherein the at least one operating parameter comprises at least one of a duration of use of the light head, a radiant power output by the light head, a pattern of light on the area of interest, or a distance of the light head from the area of interest.

19. The operating light according to claim 14, further comprising:
monitoring at least one characteristics of the area of interest; and
altering the output setting of the light head based on the monitored at least one characteristic of the area of interest.

20. The method according to claim 19, wherein the controller is configured to determine energy reflected from the area of interest or co-illumination of the area of interest based on data provided by the at least one sensor.

21. The method according to claim 14, further comprising calculating the prescribed threshold level based on patient data of a patient to be placed in the area of interest.

22. The method according to claim 21, wherein the patient data comprise at least one of an age, gender or ethnicity of a patient.

23. The method according to claim 21, wherein the patient data comprises at least one of a skin pigmentation of a patient, a medical history of the patient, a type of a medical procedure to be performed on the patient, or duration of a medical procedure to be performed on the patient.

24. The operating light according to claim 21, further comprising generating a risk index for the patient based on at least one of the at least one operating parameter of the light head or the patient parameters.

* * * * *